United States Patent
Zarate

[11] Patent Number: 5,849,036
[45] Date of Patent: Dec. 15, 1998

[54] VASCULAR GRAFT PROSTHESIS

[76] Inventor: Alfredo R. Zarate, 8128 Hamilton Spring Rd., Bethesda, Md. 20817

[21] Appl. No.: 623,693

[22] Filed: Mar. 29, 1996

[51] Int. Cl.$^6$ .................................................... A61F 2/06
[52] U.S. Cl. ................................................ 623/1; 623/12
[58] Field of Search .................... 623/1, 11, 12; 604/8; 660/36; 606/151–158

[56] References Cited

U.S. PATENT DOCUMENTS

| | | | |
|---|---|---|---|
| 3,435,824 | 4/1969 | Gamponia | 604/8 |
| 3,516,408 | 6/1970 | Montanti | 604/8 |
| 4,441,215 | 4/1984 | Kaster | 3/14 |
| 4,534,761 | 8/1985 | Raible | 604/175 |
| 4,957,508 | 9/1990 | Kaneko et al. | 623/12 |
| 5,108,417 | 4/1992 | Sawyer | 606/198 |
| 5,192,289 | 3/1993 | Jessen | 606/155 |
| 5,246,445 | 9/1993 | Yachia et al. | 623/1 |
| 5,326,373 | 7/1994 | Nagase | 623/1 |
| 5,330,528 | 7/1994 | Lazim | 623/1 |
| 5,354,310 | 10/1994 | Garnic et al. | 623/1 |
| 5,354,329 | 10/1994 | Whalen | 623/1 |
| 5,382,259 | 1/1995 | Phelps et al. | 623/1 |
| 5,387,236 | 2/1995 | Noishiki et al. | 623/1 |
| 5,399,352 | 3/1995 | Hanson | 623/1 |
| 5,411,550 | 5/1995 | Herweck et al. | 623/1 |
| 5,413,597 | 5/1995 | Krajicek | 623/1 |
| 5,423,886 | 1/1995 | Arru et al. | 623/1 |
| 5,443,499 | 8/1995 | Schmitt | 623/1 |
| 5,464,450 | 11/1995 | Buscemi et al. | 623/1 |

*Primary Examiner*—Debra S. Brittingham
*Attorney, Agent, or Firm*—Foley & Lardner

[57] ABSTRACT

A vascular graft prosthesis includes a tubular conduit for subcutaneous implantation. The tubular conduit has a first end for attachment to a vein, a second end for attachment to an artery, and an enlarged portion between the first and second ends. The enlarged portion has a diameter greater than the diameter of a remaining portion of said tubular conduit. The enlarged portion is positioned proximate the first end and spaced from the first end a distance substantially equivalent to a length of the enlarged portion.

17 Claims, 3 Drawing Sheets

VASCULAR GRAFT PROSTHESIS

BACKGROUND OF THE INVENTION

This invention relates to a novel vascular graft prosthesis. More specifically, this invention relates to a vascular graft prosthesis for use in hemodialysis or similar medical procedures.

Patients suffering from total or partial renal failure undergo hemodialysis to remove accumulated urea and other metabolic byproducts from their blood. Unclean blood is drawn from a patient's artery, passed through a dialysis machine where it is cleansed, and returned to a patient's vein. Hemodialysis requires long-term access to these blood vessels.

Arteriovenous shunts have been used in the past to provide vascular access. Quinton, Dillard, and Scribner developed such a shunt system. The Quinton-Dillard-Scribner shunt employs a silastic tube sutured to an artery. The tube is tunneled subcutaneously and exited through the skin where it connects to another silastic tube. This second silastic tube penetrates back through the skin and is sutured to a vein. During hemodialysis, the arterial silastic tube connects to an input line of a dialysis machine, and the venous silastic tube connects to the machine's return line.

Because a portion of the silastic tube remains outside the skin, patients suffer a relatively high rate of infection. Other problems associated with this shunt include skin disfigurement and frequent clotting. Moreover, because the arterial end of the shunt is connected, or anastomosed, to the end of the artery, tissues distal to the shunt do not receive adequate arterial blood supply. Thus, this shunt can only be used in peripheral arteries, such as the radial artery and the posterior tibial artery.

Various modifications of the Quinton-Dillard-Scribner shunt have been conceived. The Thomas shunt is anastomosed to the side of the femoral artery and the femoral vein, major blood vessels in the body. The Buselmeier shunt has an intravascular tip designed to decrease clotting. These modified shunts, however, still produce a high rate of infection.

Problems associated with these transcutaneous shunts led Brescia and Cimino to develop an arteriovenous fistula which remains subcutaneous post-surgery. The Brescia and Cimino procedure entails suturing the side of an artery to the side of a vein to form an H-shaped shunt. During hemodialysis, the fistula is punctured with hypodermic needles attached to the inlet and return lines of a dialysis machine.

The Brescia and Cimino fistula offers some advantages over transcutaneous shunts: the fistula has true healing and vascularization to resist/fight infection; it can remain implanted for a decade; and, because it is subcutaneous, a patient enjoys a full range of physiologic function and motion. The Brescia and Cimino fistula carries its own set of problems however: the fistula requires several weeks to mature; about twenty percent fail to develop or induce clotting after surgery; and, after repeated punctures with large bore needles, hematomas, scarring, and false aneurysms may develop.

More recently, various biological and synthetic grafts, and other medical prosthetics, have been conceived as an alternative to arteriovenous shunts and fistulas. One such medical prosthesis used in hemodialysis includes a duct with funnel-shaped ends, as disclosed in U.S. Pat. No. 3,818,511. The funnel-shaped ends are anastomosed to the ends of an artery and a vein. The funnel shape provides a smooth transition for fluid flow and has fluid dynamics advantages. Another type of medical prosthesis, for use as an aortic prosthesis, includes a corrugated tubular member with a series of annular areas separated by annular areas of smaller diameter, as disclosed in U.S. Pat. No. 3,044,497. Additional patent art disclosing medical devices and prosthetics known to applicant are the following U.S. Pat. Nos.: 4,441,215; 4,534,761; 4,957,508; 5,108,417; 5,192,289; 5,354,329; 5,413,597; and 5,443,499.

At present, more than seventy percent of the vascular grafts are made of polytetraflouroethylene (PTFE). Since the beginning of hemodialysis treatment, advances in dialysis technique have occurred, including increasing the rate of blood flow through the dialysis machine. The high blood flow rate through the machine in turn increases the velocity of the blood ejected from the venous needle into the graft. Unfortunately, graft technology has not kept up with dialysis technology. The relatively recent capability to pump blood through the dialysis machine at a high rate necessitated development of a synthetic graft designed for high velocity blood flow and for the associated high magnitude forces applied to the venous anastomosis and an early segment of the run-off vein.

The primary cause of graft failure, or dialysis access failure, is thrombosis (clotting within the blood vessel). Stenosis (narrowing of the blood vessel) causes thrombosis; studies indicate that seventy percent of thrombosed PTFE grafts exhibit stenosis. Intimal hyperplasia (hyperplastic reparative process of the intima with proliferation of endothelial and smooth muscle cells) is a leading cause of stenosis. In PTFE grafts, stenosis occurs fifty percent of the time at the venous anastomosis, and twenty percent of the time in an early segment of the run-off vein. Although PTFE grafts are prone to clotting and have shorter lifespans than Brescia-Cimino fistulas, PTFE grafts are used more frequently in patients; the Brescia-Cimino technique cannot be used on most dialysis patients because the patients generally lack usable peripheral veins, are elderly or diabetic, or suffer from arterial disease.

A major cause of intimal hyperplasia, stenosis, thrombosis and related access and vascular damage associated with PTFE grafts are the mechanical forces of blood flow through the graft—specifically high shear stress, flow turbulence, and flow separation. PTFE grafts shunt blood from a high pressure/high velocity artery to a low pressure/low velocity vein. When a patient is off dialysis, shear stress, flow turbulence, and flow separation always are present. The turbulence results from a series of factors: changes in the graft diameter (expansion at the artery-graft anastomosis and contraction at the graft-vein anastomosis); irregularities in the graft; pulsality of the cardiac cycle; and the merger of flows of different velocities at the arterial and venous anastomoses and the run-off vein. On dialysis, the shear stress, flow turbulence, and flow separation increase dramatically. Blood is suctioned from the artery by an arterial needle and returned to a vein by a venous needle at high velocity and pressure. The high velocity jet from the venous needle entrains and accelerates blood flowing in the graft. Moreover, the pulsation of the dialysis pump, the suctioning of blood by the arterial needle under negative pressure, the vortices formed around the shaft of the arterial and venous needles, and blood recirculated by the venous needle jet also contribute to increased shear stress, flow turbulence, and flow separation. The blood flow velocity, shear stress, flow turbulence, and flow separation at the venous anastomosis and run-off vein reach levels higher than in any healthy artery.

The constant exposure to high mechanical forces off dialysis, and intermittent exposure to even higher mechanical forces on dialysis, causes vascular damage. The impact of each of these mechanical forces on an access site will now be described briefly.

Shear stress and flow turbulence are directly proportional to the velocity of blood flow squared. Thus, high blood flow velocity increases shear stress and turbulence by several multiples.

Shear stress is the tractive force on the endothelium produced by blood flow. Once structural or functional endothelial damage occurs, platelets adhere to the damaged area. The platelets, endothelial cells and smooth cells release mitogenic (growth) factors that stimulate proliferation of cells and connective tissue and result in intima hyperplasia and stenosis.

Turbulent blood flow subjects the endothelium to large, multidirectional, oscillatory stresses. Vortices (clumps of blood moving rotationally and at slower velocity) and eddies (blood moving randomly and not in streamlines) impact the endothelium and causes cell distortions and attachment of clumps of blood to the endothelium. This turbulent flow also increases the fragility of the platelets. High velocity turbulence causes more harm than low velocity turbulence.

Flow separation occurs when the main body of blood flow separates from the vessel wall. Flow separation occurs at sharp curvatures in the vessel (i.e., before and after stenosis), where flows of different velocities and directions merge (i.e., at the run-off vein), where the flow either slows, stagnates, or reverses, and in areas of high turbulence.

Blood flow dynamics during hemodialysis will now be described in conjunction with FIG. 1 which schematically illustrates a conventional graft, generally indicated 10, sutured between an artery 12 and a run-off vein 14. An arterial needle 16 penetrates a patient's skin and pierces the graft 10. The tip 18 of the arterial needle 16 faces the artery 12. A venous needle 20 also penetrates a patient's skin and pierces the graft 10 so that its tip 22 faces the run-off vein 14. Blood flows from the artery 12 into the graft 10. That arterial blood is suctioned into a dialysis machine through the arterial needle 16. Clean blood reenters the graft 10 through the venous needle 20 where it is then propelled at a high velocity into the run-off vein 14. This high velocity and high turbulence flow increases the velocity of graft flow and impinges on the anastomosis 24 and the floor 23 of the run-off vein 14, resulting in flow turbulence and flow separation. Moreover, the merger of the fast-moving blood ejected from the venous needle 20 and the slow-moving blood traveling in the vein 14 increases the flow turbulence.

Not all of the blood ejected from the venous needle 20 travels into the vein 14. Some blood 25 reverses and recirculates back toward the artery 12 due to the negative pressure created by the dialysis machine at the tip 18 of the arterial needle 16. Some blood recirculates in a loop 26 in areas adjacent the graft wall downstream from the venous needle 20. Some blood recirculates in areas 28 adjacent the venous anastomosis 24. This recirculation contributes to undesirable shear stress, flow turbulence, and flow separation at the venous anastomosis and in the run-off vein.

A need thus arose for a vascular graft that decreases blood flow velocity, shear stress, flow turbulence, and flow separation. Decreasing those mechanical forces decreases the occurrence and severity of endothelial damage, increases the efficiency of hemodialysis, and decreases the incidence of intimal hyperplasia, stenosis, and thrombosis.

The difficulties suggested in the preceding are not intended to be exhaustive but rather are among many which may tend to reduce the effectiveness of prior prostheses used in connection with hemodialysis. Other noteworthy problems may also exist; however, those presented above should be sufficient to demonstrate that such methods and apparatuses appearing in the past will admit to worthwhile improvement.

Accordingly, it is therefore a general object of the invention to provide a vascular graft prosthesis which will obviate or minimize difficulties of the type previously described.

It is a specific object of the invention to provide a vascular graft prosthesis which decreases blood flow velocity at the venous anastomosis and run-off vein.

It is another object of the invention to provide a vascular graft which decreases shear stress, flow turbulence, and flow separation, both on and off dialysis, at the access site and in the run-off vein.

It is still another object of the invention to provide a vascular graft prosthesis which decreases the incidence and severity of stenosis, thrombosis, and other vascular damage that may occur during hemodialysis.

It is a further object of the invention to provide a vascular graft prosthesis which prolongs the useful life of the access site and decreases the costs related to maintaining access to the blood vessels.

It is yet a further object of the invention to provide a vascular graft prosthesis which remains stable in vivo and is durable and inexpensive to manufacture.

SUMMARY OF THE INVENTION

A preferred embodiment of the invention which is intended to accomplish at least some of the foregoing objects includes a vascular graft prosthesis having a tubular conduit. The tubular conduit has a first end for attachment to a vein, a second end for attachment to an artery, and at least one enlarged portion between the first end and the second end. The enlarged portion has a cross section larger than the cross section of a remaining portion of the tubular conduit. The enlarged section is positioned proximate the first end and spaced from the first end a distance substantially equivalent to a length of the enlarged portion. The enlarged portion may be hemispheric or fusiform in shape. In another preferred embodiment of the invention, the first end of the tubular conduit is anastomosed to a run-off vein and tapers outward towards the run-off vein in a funnel shape.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention, and, together with the general description given above and the detailed description of the preferred embodiment given below, serve to explain the principles of the invention.

DETAILED DESCRIPTION OF THE PREFERRED EMBODIMENTS

Figure 2:
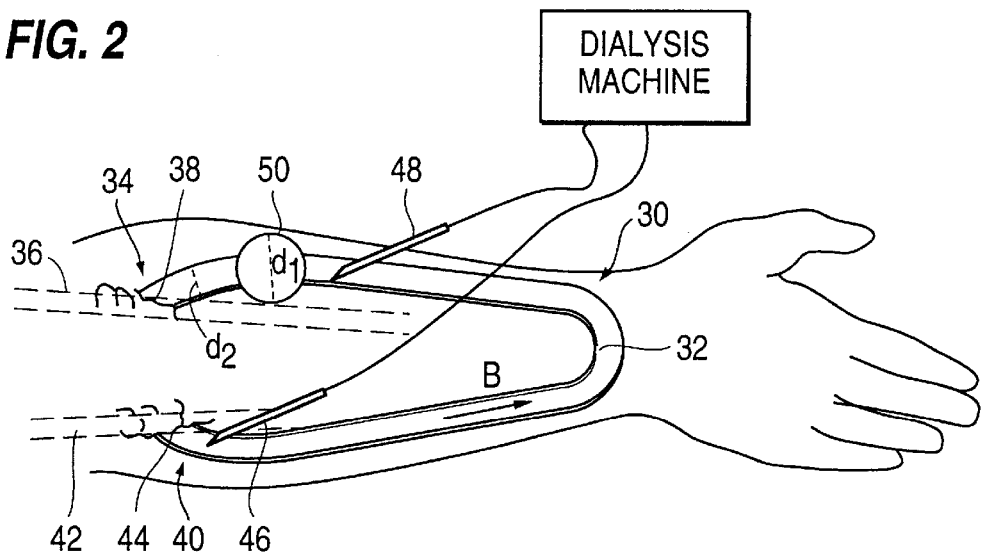
FIG. 2 is a perspective view of a preferred embodiment of a vascular graft prosthesis implanted in an arm in accordance with the invention.

Referring now to the drawings, wherein like numerals indicate like parts, and initially to FIG. 2, there will be seen a vascular graft prosthesis, generally indicated 30, for use during hemodialysis and similar medical procedures in accordance with a preferred embodiment of the invention. The vascular graft 30 includes a tubular conduit 32 having a first end 34 connected to a run-off vein 36 at a venous anastomosis 38 and a second end 40 connected to an artery 42 at an arterial anastomosis 44. On and off dialysis blood flow through the tubular conduit 32 in the direction of arrow B.

Although FIG. 2 shows the subject vascular graft prosthesis implanted subcutaneously in a patient's forearm, it will be understood that the subject invention can be implanted at any vascular access site useful for hemodialysis. It will also be understood that the first end 34 of the tubular conduit 32 may be connected to a side wall of the run-off vein 36 (end-to-side venous anastomosis) or to the end of the run-off vein 36 (end-to-end venous anastomosis). Likewise, the second end 40 of the tubular conduit 32 may be connected to a side wall of the artery 42 (end-to-side venous anastomosis) or to the end of the artery 42 (end-to-end anastomosis).

During hemodialysis, an arterial needle 46 is inserted through the patient's skin and into the tubular conduit 32. A venous needle 48 then is inserted through the patient's skin and into the tubular conduit 32 at a position between the arterial needle 46 and the enlarged portion 50. The venous needle 48 is thus upstream from the enlarged portion. Unclean blood from the patient's artery 42 is suctioned into the arterial needle 46 under negative pressure by a dialysis machine 52, and clean blood is ejected from the venous needle 48 into the tubular conduit 32 and run-off vein 36.

The tubular conduit 32 includes an enlarged portion 50 located between the venous needle 48 and the run-off vein 36. The enlarged portion 50 is preferably proximate the venous anastomosis 38. The enlarged portion 50 is spaced from the first end 34 of the tubular conduit 32 a distance substantially equivalent to the length of the enlarged portion 50. In a preferred embodiment, the enlarged portion 50 is 1–2 cm long and is located 1–2 cm from the venous anastomosis 38.

The enlarged portion 50 preferably has a spherical shape in cross section. The enlarged portion 50 has a diameter ($d_1$) greater than the diameter ($d_2$) of a remaining portion of the tubular conduit 32. For example, in a 0.6 cm diameter tubular conduit, the enlarged portion 50 preferably has a diameter in the range of 1.0–1.4 cm, although those skilled in the art may modify the diameter of the tubular conduit or the diameter of the enlarged portion to a suitable ratio.

The enlarged portion 50 may be reinforced to withstand increased pressure. For example, the wall of the tubular conduit 50 may be thickened, or rings may be mounted to, or preferably placed around the exterior surface of, the tubular conduit, as will be described in connection with FIG. 5. The subject vascular graft may be composed of DACRON®, a trademark for a polyester fiber made from polyethylene terephthalate, or TEFLON; these materials do not lose significant tensile strength following implantation.

One purpose of the subject invention is to cause energy losses, specifically velocity and pressure losses, in the blood flowing through the graft. This is accomplished by changing the diameter of the graft. Changing the graft diameter changes the velocity and pressure of the blood flow and creates controlled flow turbulence in the enlarged portion 50 of the graft 30. The higher turbulence in the enlarged portion 50 causes the desired energy losses because turbulent flow consumes more energy than laminar flow.

Figure 3:
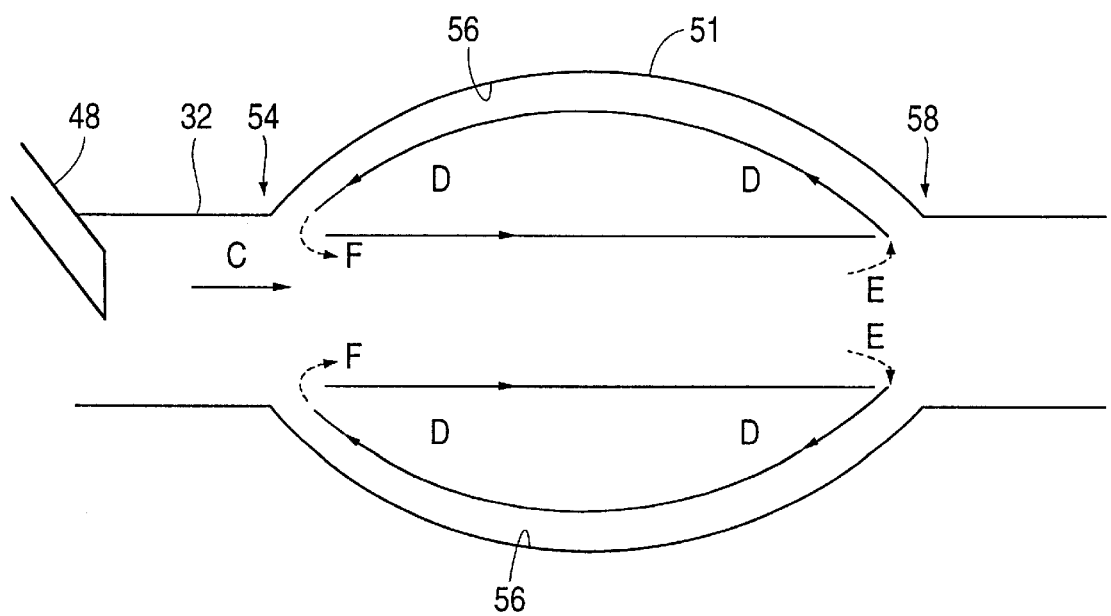
FIG. 3 is a schematic of an enlarged portion of the subject vascular graft prosthesis and illustrates blood flow dynamics within the enlarged portion.

The subject vascular graft 30 is constructed so that fast flowing blood entering the enlarged portion loses velocity. FIG. 3 shows the blood flow dynamics within an enlarged portion 51. The main jet of blood entering the enlarged portion 51 (the venous needle jet) moves in the direction of arrow C and travels at high velocity. This high velocity jet stream slows after passing through the entry 54 of the enlarged portion 51 due to the increase in diameter of the tubular conduit 32. Blood recirculating in the areas D adjacent the inner wall 56 of enlarged portion 51, also slows the velocity of the main blood flow. Blood recirculates within areas D in a direction opposite the direction C of the main blood flow. Blood flowing along the center of the enlarged portion 51 is entrained into the recirculation areas at the exit 58 of the enlarged portion 51, as shown by arrows E. At the entry 54 of the enlarged portion 51, some of the recirculating blood reenters the main blood flow, as indicated by arrows F. Upon reentry, the slower moving blood from the recirculation areas D accelerates. But, the merger of the slow moving blood traveling in the direction of arrow F and the faster moving blood traveling in the direction of arrow C generates friction and consumes kinetic energy. This slows down the velocity of the main flow overall. Because shear stress and turbulence are proportional to the velocity squared, lowering the velocity significantly decreases those mechanical forces.

Once the blood leaves the enlarged portion 51 and reenters the narrower portion of the tubular conduit 32, the velocity increases due to the reduction in diameter. But, this velocity is not as great as in the area before the enlarged portion 51 because additional kinetic and viscous losses occur. The net result is that blood enters the venous anastomosis during dialysis at a slower velocity and turbulence than it would in a graft of constant diameter.

Upon entering the run-off vein, blood flowing from the vascular graft merges with blood flowing in the run-off vein. Turbulence and flow separation occurs where these blood flow streams merge because they flow at different velocities and in difference directions. However, by slowing the velocity of the blood flow from the graft, the flow turbulence and flow separation decrease.

Figure 1:
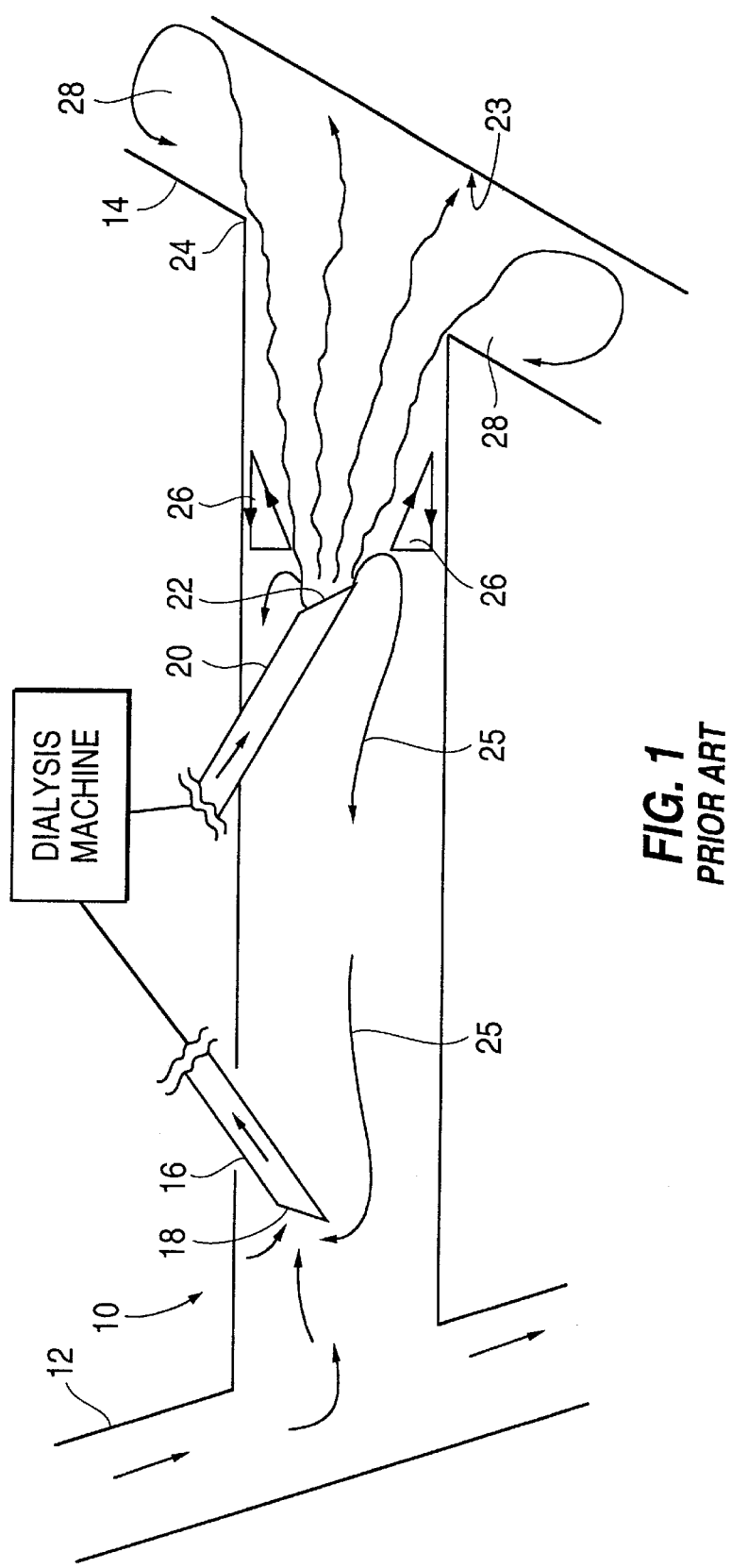
FIG. 1 is a schematic of a conventional vascular graft sutured to an artery and a run-off vein and illustrates blood flow dynamics along the graft and some resultant problems that occur during dialysis.

Another benefit of the subject vascular graft prosthesis is possible elimination, or at least a reduction, in the areas of recirculation 26 shown in FIG. 1 adjacent the venous needle. Where the venous needle 48 is positioned adjacent the enlarged portion 51, the undesirable areas of recirculation 26 in FIG. 1 would be entrained into, and eliminated or reduced by, the areas of controlled recirculation D. Any such reduction decreases the velocity and pressure, and associated harmful mechanical forces, in the tubular conduit 32 distal to the venous needle. It will be understood, however, that the venous needle may be placed at any position along tubular conduit 32 between the arterial needle and the enlarged portion, and the subject vascular graft will still provide the same benefits associated with reducing the overall blood flow velocity.

A decrease in blood flow velocity in the tubular conduit 32 past the venous needle should result in an increase in pressure in that area, according to Bernoulli's equation. Higher pressure normally causes shear stress, an undesirable effect. However, in the subject invention, although there is a decrease in blood flow velocity, any increase in pressure does not detrimentally affect the structural integrity, operation, or vascular benefits of the graft. First, pressure within the tubular conduit does not reach its maximum magnitude because of the energy losses in velocity and pressure that occur due to changes in the diameter of the graft and recirculation inside the enlarged portion. Second, elevated pressure does not cause as much endothelial damage as high velocity blood flow. Pressure does not affect turbulence, which is dependent only on velocity. Pressure does not affect flow separation. And, high systolic and diastolic arterial pressure does not correlate with a higher incidence of thrombosis in dialysis patients.

Figure 4:
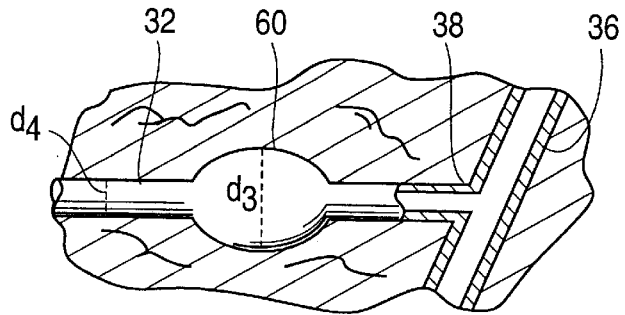
FIG. 4 is a side elevation view of a second preferred embodiment of the subject vascular graft prosthesis.

FIG. 4 shows a second preferred embodiment of the subject vascular graft prosthesis. The enlarged portion 60 has a central diameter ($d_3$) that is greater than the diameter ($d_4$) of the remaining portion of the tubular conduit 32. The enlarged portion 60 has a fusiform shape; that is, the diameter of the enlarged portion decreases from the central diameter in either direction toward the diameter of the remaining portion of the tubular conduit. Both the spherical configuration shown in FIG. 2 and the fusiform configuration shown in FIG. 4 enjoy the benefits discussed in connection with FIG. 3.

Figure 5:
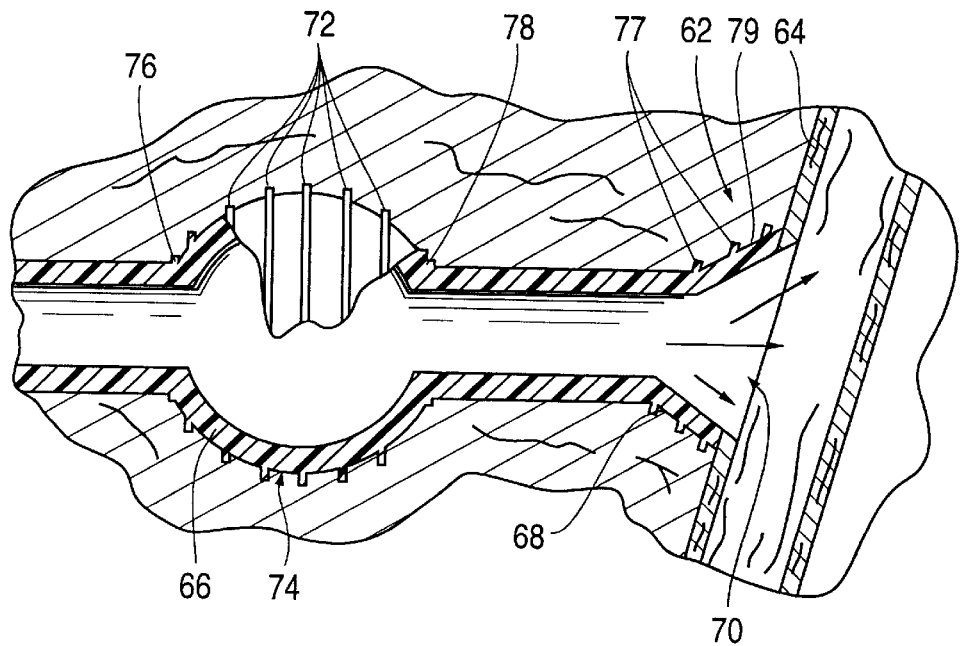
FIG. 5 is a side elevation view of a third preferred embodiment of the subject vascular graft prosthesis.

A third preferred embodiment of the subject vascular graft prosthesis shown in FIG. 5 includes a first end, generally indicated 62, for attachment to a vein 64, a second end (not shown) for attachment to an artery, and a generally spherical enlarged area 66. The first end 62 has a funnel portion 68 which gradually tapers outward as it nears the run-off vein 64 so that a funnel mouth 70 of the first end 62 opens into the vein 64. The funnel portion 68 has a length preferably ranging from 1.0–1.4 cm. The funnel portion 68 results in an increased diameter at the venous anastomosis which has positive effects on blood flow dynamics. The increased diameter decreases the blood flow velocity, flow turbulence, and wall shear stress at the venous anastomosis and at the run-off vein 64.

The funnel portion 68 of the subject vascular graft prosthesis provides advantages over conventional grafts. Conventional grafts typically are anastomosed to a vein at either a ninety degree or a forty-five degree angle, depending on the patient anatomy. In cases where the graft is anastomosed to the vein at a forty-five degree angle, the end of the graft tube is cut at an angle and thus that end has a larger diameter than the remaining portion of the graft tube. However, in cases where the angle of insertion is at ninety degrees, the graft end anastomosed to the vein has a diameter equal to the diameter of the remaining portion of the graft tube.

In the subject invention, the funnel-shaped graft end will always have a diameter greater than the diameter of the remaining portion of the tube, regardless of the angle of insertion. At a ninety degree angle of insertion, the funnel portion 68 tapers outward toward the run-off vein to create a large diameter. Where the funnel portion 68 is tailored for a forty-five degree angle of insertion, the ratio of the graft diameter at the anastomosis and the graft diameter in the tubular conduit is larger than the ratio possible in conventional grafts. As discussed above, increasing the diameter of the graft at the venous anastomosis reduces the blood flow velocity, flow turbulence, and wall shear stress at the venous anastomosis and at the run-off vein.

The subject invention may also include reinforcement rings 72 which encircle an exterior surface 74 of the enlarged portion 66. Reinforcement rings operate to maintain the shape of the enlarged portion 66 when the patient is off dialysis. The reinforcement rings 72 are preferably composed of a metallic or rigid plastic material. Reinforcement rings 72 may also encircle either end 76 and 78 of the enlarged portion 66 to stabilize the tubular conduit at the entry and exit of the enlarged portion 66. Further, reinforcement rings 77 may encircle the exterior surface 79 of the funnel portion 68. Reinforcement of the enlarged portion 66 and of the funnel portion 68 may also be accomplished by thickening the graft wall at those portions. It will be understood by those skilled in the art that reinforcement rings may be mounted within the tubing material forming the enlarged portion, funnel portion, and remaining portion of the tubular conduit, or in any other suitable arrangement designed to maintain the structural integrity of the graft.

Figure 6:
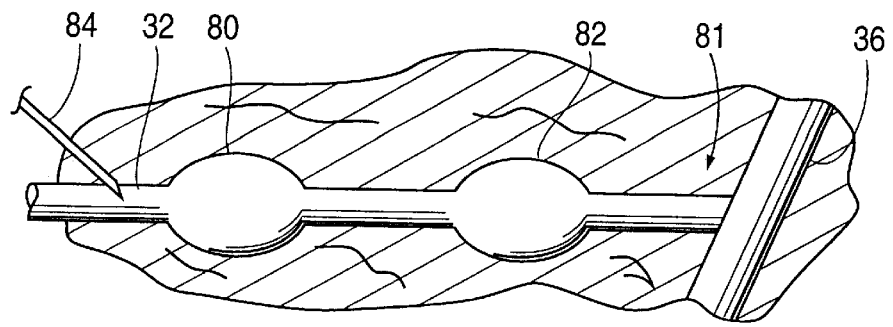
FIG. 6 is a side elevation view of a fourth preferred embodiment of the subject vascular graft prosthesis and includes two enlarged portions.

In another aspect of the invention, as shown in FIG. 6, the tubular conduit may include two enlarged portions 80 and 82 positioned in series along the tubular conduit 32 proximate the first end 81 and proximate, but spaced from, each other. Each enlarged portion 80 and 82 has a diameter greater than the diameter of the remaining portion of the tubular conduit 32. In this embodiment, during dialysis, a venous needle 84 is placed upstream from both of the enlarged portions 80 and 82. In other words, the venous needle is placed between the arterial needle and the enlarged portion located furthest from the venous anastomosis.

Although a vascular graft prosthesis could have a series of enlarged portions, it is preferable that the subject vascular graft include only one or two enlarged portions for several reasons. Some of these reasons include: the more enlarged portions, the more difficult it is to declot the graft; more enlarged portions requires a long incision and a large diameter channel in a patient's tissue to implant the graft and accommodate the enlarged portions; more enlarged portions may lead to excessive stretching of the skin; and more enlarged portions means fewer optimal sites for insertion of the venous needle.

A method of hemodialyzing a patient in accordance with the subject invention includes providing a tubular conduit having an enlarged portion positioned between a first end and a second end of said tubular conduit. The enlarged portion is positioned proximate the first end, as discussed in connection with FIG. 2. The tubular conduit is implanted beneath skin of the patient to provide vascular access. The first end of the tubular conduit is anastomosed to a run-off vein and the second end is anastomosed to an artery. The skin and the tubular conduit are then pierced with an arterial needle and a venous needle. The venous needle is positioned between the arterial needle and the enlarged portion so that a tip of the venous needle points toward the enlarged portion. The arterial and venous needles are connected to a dialysis machine. Blood is drawn into the dialysis machine via the arterial needle, and cleansed blood is returned to the tubular conduit via the venous needle at high velocity. The velocity of blood flowing through the tubular conduit toward the run-off vein slows in said enlarged portion. This reduces the mechanical forces of shear stress, flow turbulence, and flow separation, as discussed above, and thereby reduces the incidence of intimal hyperplasia, stenosis, thrombosis, and other vascular and access damage.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. A vascular graft prosthesis comprising:
    a tubular conduit for passage of blood therethrough, said tubular conduit having
        a first end for attachment to a first blood vessel,
        a second end for attachment to a second blood vessel, and
        no more than two, fluid-impermeable, enlarged portions positioned between said first end and said second end, each of said enlarged portions having an inner diameter greater than an inner diameter of a remaining portion of said tubular conduit, each of said enlarged portions being in fluid communication with said tubular conduit so that blood passing through said tubular conduit in a direction from said second end to said first end is entrained into, and recirculates within, each of said enlarged portions to slow the overall velocity of the blood through said tubular conduit.

2. A vascular graft prosthesis as defined in claim 1 wherein said no more than two enlarged portions comprise a single enlarged portion, and said single enlarged portion is positioned proximate said first end and spaced from said first end a distance substantially equivalent to a length of said single enlarged portion.

3. A vascular graft prosthesis as defined in claim 1 wherein said enlarged portion has a spherical shape in cross section.

4. A vascular graft prosthesis as defined in claim 1 wherein each of said enlarged portions is fusiform in shape.

5. A vascular graft prosthesis as defined in claim 1 wherein said first end has a funnel portion with a funnel mouth opening away from said enlarged portion.

6. A vascular graft prosthesis as defined in claim 5 and further comprising reinforcement rings encircling said funnel portion.

7. A vascular graft prosthesis as defined in claim 1 wherein said first end tapers outward away from said enlarged portion.

8. A vascular graft prosthesis as defined in claim 1 wherein said first end is connectable to a side wall of a run-off vein to form an end-to-side venous anastomosis.

9. A vascular graft prosthesis as defined in claim 1 wherein said second end is connectable to a side wall of an artery to form an end-to-side arterial anastomosis.

10. A vascular graft prosthesis as defined in claim 1 and further comprising at least one reinforcement ring encircling said enlarged portion.

11. A vascular graft prosthesis as defined in claim 10 wherein said at least one reinforcement ring is mounted to an exterior surface of said enlarged portion.

12. A vascular graft prosthesis as defined in claim 1 and further comprising reinforcement rings encircling said tubular conduit at both ends of said enlarged portion.

13. A vascular graft prosthesis as defined in claim 12 wherein said reinforcement rings are mounted to an exterior surface of said tubular conduit.

14. A vascular graft prosthesis as defined in claim 1, wherein said enlarged portions are spaced from each other.

15. A vascular graft prosthesis as defined in claim 1 wherein said no more than two enlarged portions comprise a single enlarged portion.

16. A vascular graft prosthesis, comprising:
    a tubular conduit for subcutaneous implantation between two blood vessels, said tubular conduit having
        a first end for attachment to a first blood vessel,
        a second end for attachment to a second blood vessel, and
        no more than two enlarged portions positioned between said first end and said second end, each of said enlarged portions having an inner diameter greater than an inner diameter of a remaining portion of said tubular conduit, each of said enlarged portions being in fluid communication with said tubular conduit so that blood passing through said tubular conduit in a direction from said second end to said first end is entrained into, and recirculates within, each of said enlarged portions to slow the overall velocity of the blood through said tubular conduit.

17. A vascular graft prosthesis as defined in claim 16 wherein each of said enlarged portions is nonextendible in an axial direction.

* * * * *